(12) United States Patent
Bolze et al.

(10) Patent No.: US 11,850,238 B2
(45) Date of Patent: Dec. 26, 2023

(54) USE OF A THIENOPYRIDONE DERIVATIVE IN THE TREATMENT OF ADRENOLEUKODYSTROPHY OR ADRENOMYELONEUROPATHY

(71) Applicant: POXEL, Lyons (FR)

(72) Inventors: Sébastien Bolze, Massieux (FR); Pascale Fouqueray, Sins (CH); Sophie Hallakou-Bozec, Antony (FR)

(73) Assignee: POXEL, Lyons (FR)

( * ) Notice: Subject to any disclaimer, the term of this patent is extended or adjusted under 35 U.S.C. 154(b) by 0 days.

(21) Appl. No.: 17/914,372

(22) PCT Filed: Mar. 26, 2021

(86) PCT No.: PCT/EP2021/057988
§ 371 (c)(1),
(2) Date: Sep. 26, 2022

(87) PCT Pub. No.: WO2021/191435
PCT Pub. Date: Sep. 30, 2021

(65) Prior Publication Data
US 2023/0112080 A1    Apr. 13, 2023

(30) Foreign Application Priority Data
Mar. 26, 2020   (EP) .................................... 20166035

(51) Int. Cl.
*A61K 31/4365* (2006.01)
*A61P 25/28* (2006.01)

(52) U.S. Cl.
CPC .......... *A61K 31/4365* (2013.01); *A61P 25/28* (2018.01)

(58) Field of Classification Search
CPC ............................ A61K 31/4365; A61P 25/28
See application file for complete search history.

(56) References Cited

U.S. PATENT DOCUMENTS

2023/0120204 A1   4/2023   Bolze et al.
2023/0149370 A1   5/2023   Bolze et al.

FOREIGN PATENT DOCUMENTS

| EP | 2 679 591 | 1/2014 |
| EP | 3 335 730 | 6/2018 |
| WO | WO 2009/124636 | 10/2009 |
| WO | WO 2018/107056 | 6/2018 |

OTHER PUBLICATIONS

Kochova (X-Linked Adrenoleukodystrophy: Diagnostic and Therepeutic Approach, Mini Review, vol. 2, Issue 3, Mar. 2017).*
Written Opinion in International Application No. PCT/EP2021/057988, dated Jun. 24, 2021, pp. 1-10.
International Preliminary Report on Patentability in International Application No. PCT/EP2021/057988, dated Jul. 5, 2022, pp. 1-16.
Singh, J. et al. "Metformin-induced mitochondrial function and ABCD2 up-regulation in X-linked adrenoleukodystrophy involves AMP-activated protein kinase" *Journal of Neurochemistry*, 2016, pp. 86-100, vol. 138.
Kim, J. et al. "AMPK activators: mechanisms of action and physiological activities" *Experimental & Molecular Medicine*, published online Apr. 1, 2016, pp. 1-12, vol. 48, e224.
Steinberg, G. R. et al. "AMP-activated protein kinase: the current landscape for drug development" *Nature Reviews/Drug Discovery*, Jul. 2019, pp. 527-551, vol. 18.
Pending claims for U.S. Appl. No. 17/915,120, filed Sep. 28, 2022, pp. 1-2.

* cited by examiner

*Primary Examiner* — Kathrien A Hartsfield
(74) *Attorney, Agent, or Firm* — SALIWANCHIK, LLOYD & EISENSCHENK

(57) ABSTRACT

The invention relates to the use of a thienopyridone derivative, or a pharmaceutical composition comprising the same, in the treatment of genetic neurodegenerative diseases selected from adrenoleukodystrophy (ALD) and adrenomyeloneuropathy (AMN).

19 Claims, 7 Drawing Sheets

****, p<0.001 vs ctrl AMN fibroblasts
*, p<0.05 vs ctrl AMN fibroblasts

USE OF A THIENOPYRIDONE DERIVATIVE IN THE TREATMENT OF ADRENOLEUKODYSTROPHY OR ADRENOMYELONEUROPATHY

CROSS-REFERENCE TO RELATED APPLICATION

This application is the U.S. national stage application of International Patent Application No. PCT/EP2021/057988, filed Mar. 26, 2021.

TECHNICAL FIELD

The invention relates to the use of a thienopyridone derivative in the treatment of genetic neurodegenerative diseases selected from adrenoleukodystrophy (ALD) and adrenomyeloneuropathy (AMN).

TECHNICAL BACKGROUND

Adrenoleukodystrophy and adrenomyeloneuropathy are neurodegenerative genetic diseases. X-linked adrenoleukodystrophy (ALD) is a genetic disease linked to the X chromosome. Three main phenotypes are seen in affected males. The childhood cerebral form manifests usually between ages 4 and 8 years. It initially resembles attention deficit disorder or hyperactivity. Progressive central demyelination with impairment of cognition, behavior, vision, hearing, and motor function follow the initial symptoms and often lead to total disability within 2 years. The second phenotype, adrenomyeloneuropathy (AMN) which is the adult form of ALD, manifests most commonly in the late twenties as progressive paraparesis, sphincter disturbances, sexual dysfunction, and often, impaired adrenocortical function. Moreover, AMN patients generally have spinal cord dysfunction, which leads to the initial symptoms that include difficulties in walking or a change in the walking pattern. All symptoms are progressive over decades. Particularly, AMN can be broken down into two general clinical forms: AMN with cerebral involvement where the spinal cord and brain are both affected, and AMN without cerebral involvement where only the spinal cord is affected. The third phenotype is Addison's disease, which is present with primary adrenocortical insufficiency between age 2 years and adulthood and most commonly by age 7.5 years, without evidence of neurologic abnormality.

X-linked adrenoleukodystrophy (ALD) is caused by mutations in the ABCD1 gene. The ABCD1 gene provides instructions for producing the adrenoleukodystrophy protein (ALDP). ALDP is located in the membranes of cell structures called peroxisomes. Peroxisomes are small sacs within cells that process many types of molecules. ALDP brings a group of fats called very long-chain fatty acids (VLCFAs) into peroxisomes, where they are broken down. The mutations that cause adrenoleukodystrophy prevent the production of any ALDP in about 75 percent of people with this disorder. With little or no functional ALDP, VLCFAs are not broken down, and they build up in the body. This leads to elevated levels of very long chain fatty acids (VLCFA) and reduced VLCFA oxidation in peroxisomes. Lipids containing VLCFA accumulate in all tissues; however, the brain, spinal cord, adrenal cortex and the Leydig cells of the testis have the greatest increase of VLCFA. The accumulation of these fats may be toxic to the adrenal glands and to the fatty layer of insulation (myelin) that surrounds many nerves in the body. In childhood cerebral ALD, not only do cells undergo demyelination, but there is also an inflammatory response, all of which destroy the brain. The inflammatory process destroys the myelin, causing relentless progressive deterioration to a vegetative state or death, usually within five years.

Adrenomyeloneuropathy (AMN) is the adult onset of adrenoleukodystrophy (ALD). As ALD, AMN is characterized by ABCD1 gene mutation, that results in impaired peroxisome function with accumulation of very long chain fatty acids (VLCFA) and demyelination. Unlike ALD, which is a rapidly progressive fatal disorder of early childhood, AMN is a slowly progressive disorder of adulthood that causes dysfunction of the adrenal gland, spinal cord (myelopathy), and peripheral nerves (neuropathy).

There is no effective treatment for X-ALD; haematopoietic stem cell bone marrow transplantation (HSCT) may reduce the progression of ALD in some patients if done when neurological symptoms first appear. However, HSCT is also associated with substantial morbidity and mortality.

The current ways of treating these diseases are essentially aimed at relieving patients' symptoms. For instance, one of the possible symptoms of patients with AMN is adrenal insufficiency, so the focus will be on the treatment of this adrenal insufficiency with steroid replacement therapy.

Recently, some authors have reported the loss of AMPKα1 in ALD patients and suggested that metformin could be useful for treating these patients by activating AMPK (J. Singh et al., Journal of Neurochemistry, 138, 86-100, 2016). However, metformin is known to induce lactic acidosis as a side effect. Additionally, its efficacy is observed in cultured fibroblasts at a dose of at least 100 µM and, in ABCD2 KO mice, when orally administered at 100 mg/kg.

Hence, there remains the need for alternative compounds that would be useful in the treatment of ALD and AMN at lower doses and/or with reduced side effects.

The inventors have shown that specific thienopyridone derivatives could meet this need. These compounds were broadly disclosed as AMPK activators in WO 2014/001554 but it has never been suggested so far to use them in the treatment of ALD and AMN. They have proven to be direct activators of various AMPK isoforms including the β1 subunit, which makes their efficacy in the treatment of these conditions all the more so surprising that it is known that direct activators of AMPK provide metabolic effects that are different from those obtained with indirect activators of AMPK such as metformin.

More specifically, the inventors discovered that these thienopyridone derivatives could restore the healthy phenotype or improve the phenotype of these diseases.

These thienopyridone derivatives act to reduce the accumulation of very long-chain fatty acids (VLCFAs). It was also found that when cells are cultured in the presence of a thienopyridone derivative of formula (I), the expression of an alternative protein (ABCD2), related to ALDP (with a sequence very close to that of ALDP) is induced. Since ALDP is deleted in ALD and AMN, the induction of a related protein appears to underlie the mechanism by which a thienopyridone derivative of formula (I) can ameliorate the disease phenotype in this model system. Thus, these thienopyridone derivatives, through overexpression of this protein, allow for the reduction of fatty acid accumulation.

SUMMARY OF THE INVENTION

This invention relates to the treatment of adrenoleukodystrophy and/or adrenomyeloneuropathy with thienopyridone derivatives. More specifically, the invention relates to a thienopyridone derivative of Formula (I):

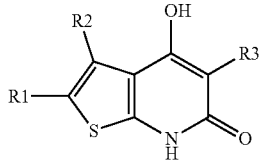

(I)

wherein:
R1 represents a hydrogen atom or a halogen atom,
R2 represents an indanyl or tetralinyl group, substituted or not by one or more (e.g. 2, 3, 4, 5, 6 or 7) groups selected from halogen atoms, alkyl groups, hydroxy, alkoxy groups, amino, mono- or di-alkylamino groups, carboxy groups, alkyloxycarbonyl groups, mono- or di-alkylaminocarbonyl groups, carboxamide, cyano, alkylsulfonyl and trifluoromethyl groups,
R3 represents an aryl group, substituted or not by one or more (e.g. 2, 3, 4 or 5) atoms or groups selected from halogen atoms, alkyl groups, hydroxy, alkoxy groups, aralkyloxy groups, amino, mono- or di-alkylamino groups, carboxy groups, alkyloxycarbonyl groups, mono- or di-alkylaminocarbonyl groups, carboxamide, cyano, alkylsulfonyl and trifluoromethyl groups,
or its pharmaceutically acceptable salts and/or solvates, or a pharmaceutical composition comprising the same, for use in the treatment of ALD and/or AMN.

The present invention also relates to a method for the treatment of ALD and/or AMN, comprising administering to a subject in need thereof an effective amount of a thienopyridone derivative as described above, or a pharmaceutical composition comprising an effective amount of a thienopyridone derivative as described above and a pharmaceutically acceptable support, to a patient in need thereof.

The present invention also relates to the use of a thienopyridone derivative as described above, or a pharmaceutical composition comprising the same, for the manufacture of a medicament for the treatment of ALD and/or AMN.

Six situations were studied: Healthy control/AMN without treatment/AMN+PXL770 (5 μM)/AMN+PXL770 (10 μM)/ AMN+PXL770 (25 μM)/AMN+PXL770 (50 μM).

Figure 6:
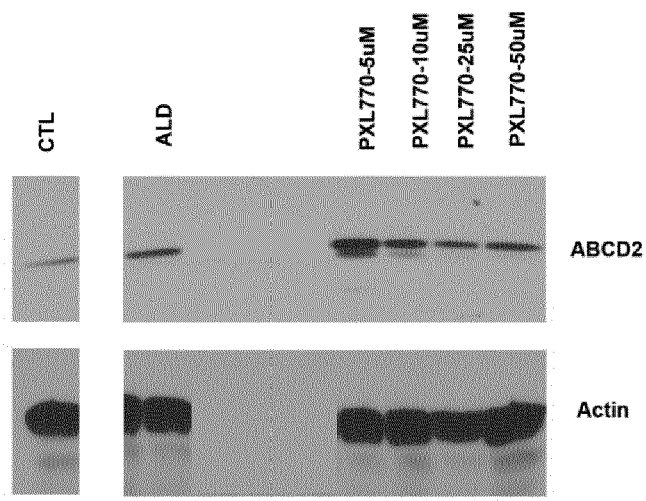

FIG. 6 shows the level of expression of ABCD2 in ALD fibroblasts when they are cultured with or without the presence of PXL770.

Figure 7:
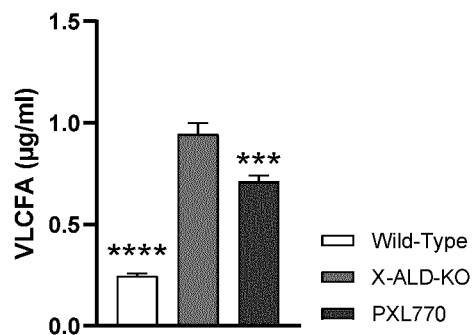

FIG. 7 shows hexacosanoic acid levels in brain cortex of X-ALD mice treated with PXL770, compared to untreated X-ALD mice and to wild-type mice.

Figure 8:
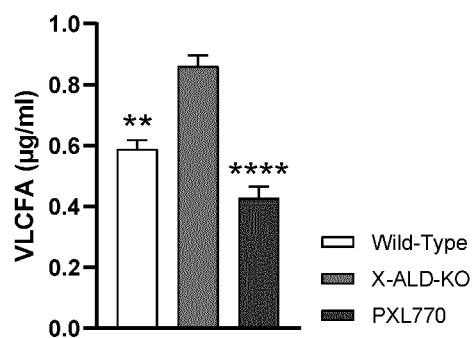

FIG. 8 shows hexacosanoic acid levels in the plasma of X-ALD mice treated with PXL770, compared to untreated X-ALD mice and to wild-type mice.

Figure 9:
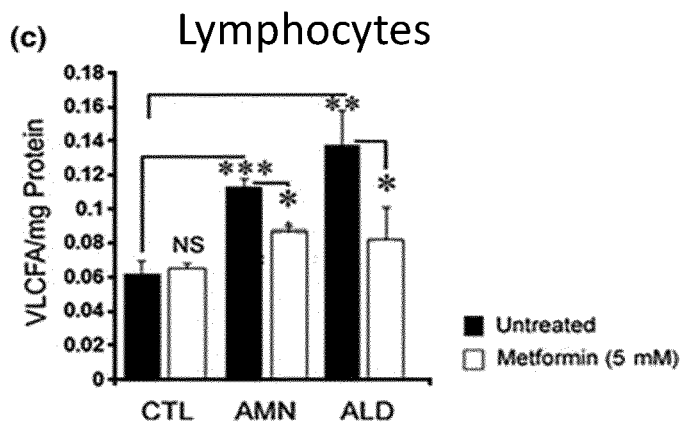

FIG. 9 shows the level of hexacosanoic acid in AMN patient-derived fibroblasts and lymphocytes when they are treated or not with metformin.

Figure 10:
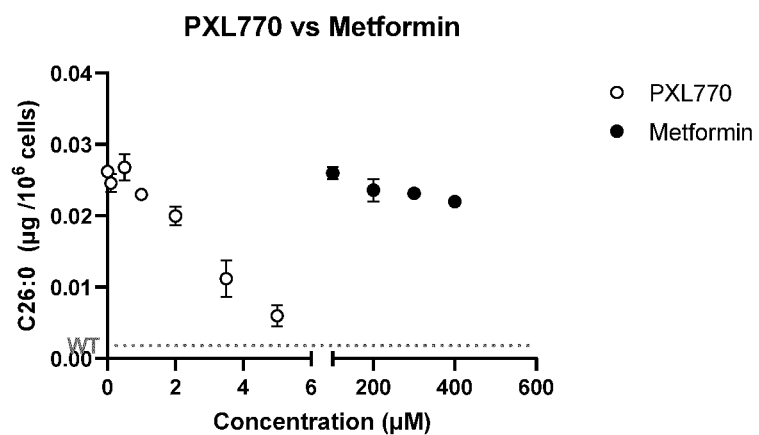

FIG. 10 shows a head-to-head comparison between PXL770 and metformin on hexacosanoic acid levels in AMN patient-derived fibroblasts.

Figure 11:

FIG. 11 shows the level of expression of ABCD2 in AMN and ALD fibroblasts when they are cultured with or without the presence of metformin.

Figure 12:
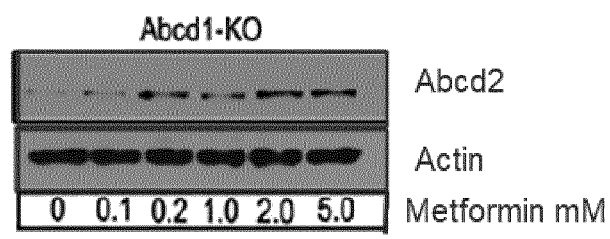

FIG. 12 shows the level of expression of ABCD2 in ALD-KO mouse brain cortex mixed glial cells when they are cultured with or without the presence of metformin.

Figure 13:
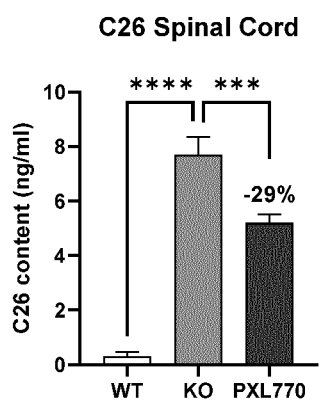

FIG. 13 shows hexacosanoic acid levels in spinal cord of X-ALD mice treated with PXL770, compared to untreated X-ALD mice and to wild-type mice.

Figure 14:
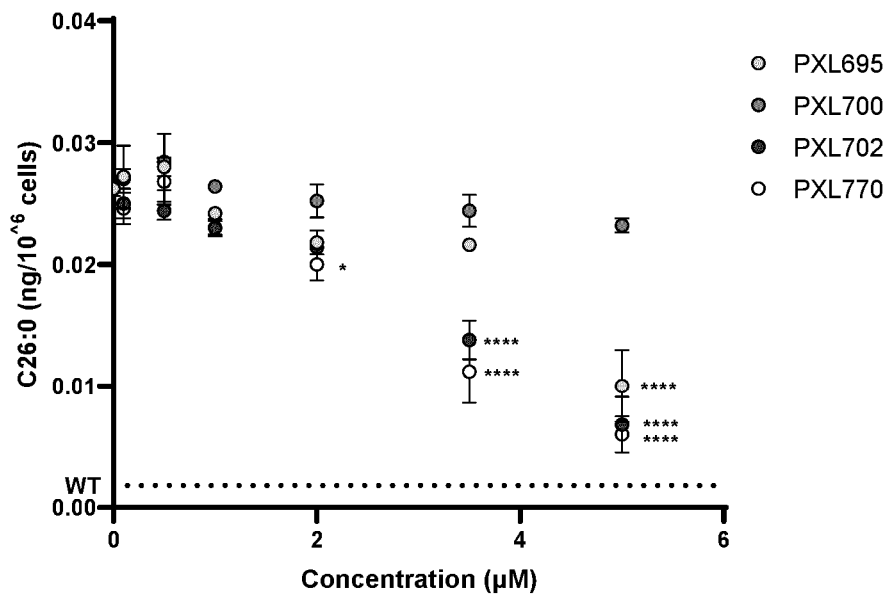

FIG. 14 shows the level of hexacosanoic acid in AMN patient-derived fibroblasts when they are treated with various doses of compounds according to this invention.

Figure 15:
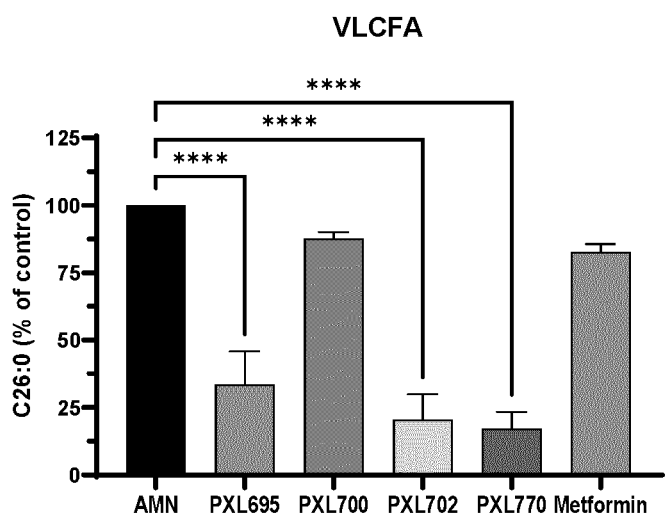

FIG. 15 shows the level of hexacosanoic acid in AMN patient-derived fibroblasts when they are treated with various compounds according to this invention, compared to metformin.

DETAILED DESCRIPTION OF THE INVENTION

Definitions

As used herein, the following terms are defined with the following meanings unless explicitly stated otherwise.

The term "halogen atom" refers to an atom selected from fluorine, chlorine, bromine and iodine atoms.

The term "alkyl group" refers to a linear or branched saturated chain of 1 to 5 carbon atoms, such as methyl, ethyl, n-propyl, iso-propyl, n-butyl, sec-butyl, iso-butyl or tert-butyl. Preferably, alkyl groups are linear or branched saturated chains of 1 to 3 carbon atoms, such as methyl, ethyl, n-propyl or iso-propyl groups.

The term "aryl group" refers to a C6-C18 aromatic group, such as phenyl or naphthyl group, optionally substituted by one or more atoms or groups selected from halogen atoms, alkyl groups, hydroxy (OH), alkyloxy groups, amino ($NH_2$), mono- or di-alkylamino groups, carboxy (COOH), alkyloxycarbonyl groups, mono- or di-alkylaminocarbonyl groups, carboxamide ($CONH_2$), cyano (CN), alkylsulfonyl groups and trifluoromethyl ($CF_3$). More specifically, the aryl group can be substituted or not by fluorine, chlorine, bromine atoms, hydroxy, methoxy, ethoxy, amino, dimethylamino, diethylamino, methyl, ethyl, n-propyl, n-butyl, iso-propyl, sec-butyl, iso-butyl, tert-butyl, carboxy, methoxycarbonyl, ethoxycarbonyl, carboxamide, dimethylaminocarbonyl, methylaminocarbonyl, cyano, methyl sulfonyl, or trifluoromethyl group.

The term "aralkyl group" refers to alkyl group as defined above, a hydrogen atom of which is replaced by an aryl group as defined above. An example of an aralkyl group is a benzyl group. The term "alkyloxy" (or "alkoxy") group refers to an alkyl group as defined above linked to the rest of the molecule through an oxygen atom. Among alkyloxy groups mention can be made of methoxy and ethoxy groups.

The term "aralkyloxy" group refers to an aralkyl group as defined above linked to the rest of the molecule through an oxygen atom. Among aralkyloxy groups mention can be made of the benzyloxy group.

The term "alkylamino group" refers to an alkyl group as defined above linked to the rest of the molecule through a nitrogen atom. Among alkylamino groups mention can be made of dimethylamino and diethylamino groups.

The term "alkyloxycarbonyl group" refers to an alkyloxy group as defined above linked to the rest of the molecule through a carbonyl group.

The term "alkylaminocarbonyl group" refers to an alkylamino group as defined above linked to the rest of the molecule through a carbonyl group.

The term "alkylsulfonyl" refers to an alkyl as defined above linked to the rest of the molecule through a SO2 group. Among alkylsulfonyl groups mention can be made of methylsulfonyl and ethylsulfonyl groups.

"Solvates" of the compounds are taken in the present invention to mean adductions of inert solvent molecules onto the compounds which form owing to their mutual attractive force. Solvates are, for example, hydrates or alcoholates.

This invention pertains to specific uses of thienopyridone derivatives of Formula (I):

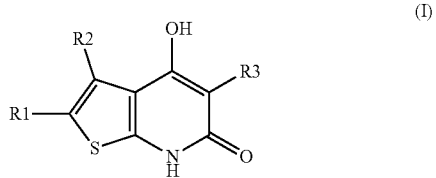

wherein:
R1 represents a hydrogen atom or a halogen atom,
R2 represents an indanyl or tetralinyl group, substituted or not by one or more (e.g. 2, 3, 4, 5, 6 or 7) groups selected from halogen atoms, alkyl groups, hydroxy, alkoxy groups, amino, mono- or di-alkylamino groups, carboxy groups, alkyloxycarbonyl groups, mono- or di-alkylaminocarbonyl groups, carboxamide, cyano, alkylsulfonyl and trifluoromethyl groups,
R3 represents an aryl group, substituted or not by one or more (e.g. 2, 3, 4 or 5) atoms or groups selected from halogen atoms, alkyl groups, hydroxy, alkoxy groups, aralkyloxy groups, amino, mono- or di-alkylamino groups, carboxy groups, alkyloxycarbonyl groups, mono- or di-alkylaminocarbonyl groups, carboxamide, cyano, alkylsulfonyl and trifluoromethyl groups, or their pharmaceutically acceptable salts and/or solvates.

In a particular embodiment, at least one of the following conditions is met and preferably all of them:
R1 represents a halogen atom, in particular a chlorine atom,
R2 is unsubstituted or substituted by 1 or 2 substituents including at least one hydroxy group,
R2 is a tetralinyl group,
R3 represents a phenyl, which is unsubstituted or substituted by 1 or 2 substituents,
the compound of formula (I) is in the form of a salt, preferably a sodium or potassium salt, more preferably a potassium salt,
the compound of formula (I) is in the form of a solvate, preferably a hydrate, more preferably a monohydrate.

Still preferably, at least one of the following conditions is met and preferably all of them:
R1 represents a halogen atom, in particular a chlorine atom,
R2 is substituted by 1 or 2 substituents including at least one hydroxy group,
R2 is a tetralinyl group,
R3 represents a phenyl group, which is unsubstituted,
the compound of formula (I) is in the form of a salt, preferably a sodium or potassium salt, more preferably a potassium salt,
the compound of formula (I) is in the form of a solvate, preferably a hydrate, more preferably a monohydrate.

In another embodiment, at least one of the following conditions is met and preferably all of them:
R1 represents a halogen atom, in particular a chlorine atom,
R2 is substituted by 1 or 2 substituents including at least one hydroxy group,
R2 is an indanyl group,
R3 represents a phenyl group, which is unsubstituted or substituted by 1 or 2 substituents.

Examples of compounds of formula (1) are the following:
2-chloro-4-hydroxy-3-indan-5-yl-5-phenyl-7H-thieno[2,3-b]pyridin-6-one
2-chloro-5-(4-fluorophenyl)-4-hydroxy-3-indan-5-yl-7H-thieno[2,3-b]pyridin-6-one
2-chloro-4-hydroxy-3-indan-5-yl-5-(3-methoxyphenyl)-7H-thieno[2,3-b]pyridin-6-one
2-chloro-4-hydroxy-3-indan-5-yl-5-(4-methoxyphenyl)-7H-thieno[2,3-b]pyridin-6-one
3-(2-chloro-4-hydroxy-3-indan-5-yl-6-oxo-7H-thieno[2,3-b]pyridin-5-yl)benzonitrile
2-chloro-4-hydroxy-3-indan-5-yl-5-(3-methylphenyl)-7H-thieno[2,3-b]pyridin-6-one
2-chloro-5-(4-fluorophenyl)-4-hydroxy-3-(4-hydroxyindan-5-yl)-7H-thieno[2,3-b]pyridin-6-one
2-chloro-5-(3-fluorophenyl)-4-hydroxy-3-(4-hydroxyindan-5-yl)-7H-thieno[2,3-b]pyridin-6-one
2-chloro-4-hydroxy-3-(4-hydroxyindan-5-yl)-5-phenyl-7H-thieno[2,3-b]pyridin-6-one 2-chloro-5-(2-fluorophenyl)-4-hydroxy-3-(4-hydroxyindan-5-yl)-7H-thieno[2,3-b]pyridin-6-one
2-chloro-4-hydroxy-3-(5-hydroxytetralin-6-yl)-5-phenyl-7H-thieno[2,3-b]pyridin-6-one
3-(2-chloro-4-hydroxy-6-oxo-3-tetralin-6-yl-7H-thieno[2,3-b]pyridin-5-yl)benzonitrile
Trisodium 2-chloro-3-(5-oxidotetralin-6-yl)-5-phenyl-thieno[2,3-b]pyridine-4,6-diolate
2-chloro-4-hydroxy-5-phenyl-3-tetralin-6-yl-7H-thieno[2,3-b]pyridin-6-one
2-chloro-5-(4-fluorophenyl)-4-hydroxy-3-(5-hydroxytetralin-6-yl)-7H-thieno[2,3-b]pyridin-6-one
disodium 2-chloro-3-(5-oxidotetralin-6-yl)-6-oxo-5-phenyl-7H-thieno[2,3-b]pyridin-4-olate
2-chloro-4-hydroxy-3-(5-hydroxytetralin-6-yl)-5-(3-methylphenyl)-7H-thieno[2,3-b]pyridin-6-one 2-chloro-4-hydroxy-3-(5-hydroxytetralin-6-yl)-5-(4-methylphenyl)-7H-thieno[2,3-b]pyridin one 2-chloro-5-(3-fluorophenyl)-4-hydroxy-3-(5-hydroxytetralin-6-yl)-7H-thieno[2,3-b]pyridin one sodium 2-chloro-3-(5-hydroxytetralin-6-yl)-6-oxo-5-phenyl-7H-thieno[2,3-b]pyridin-4-olate potassium 2-chloro-3-(5-hydroxytetralin-6-yl)-6-oxo-5-phenyl-7H-thieno[2,3-b]pyridin olate.

The compounds of formula (I) may generally be prepared as disclosed in WO 2014/001554.

Examples of such compounds include:

PXL770 which is the monohydrate potassium salt of 2-chloro-4-hydroxy-3-(5-hydroxytetralin-6-yl)-5-phenyl-7H-thieno[2,3-b]pyridin-6-one corresponding to the following structure of Formula (Ia):

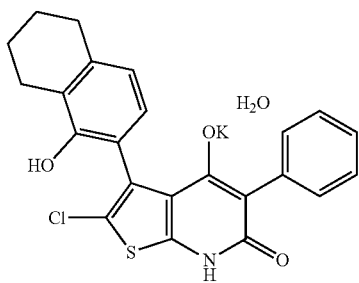

(Ia)

2-chloro-5-(3-fluorophenyl)-4-hydroxy-3-(4-hydroxyindan-5-yl)-7H-thieno[2,3-b] pyridin-6-one having Formula (Ib):

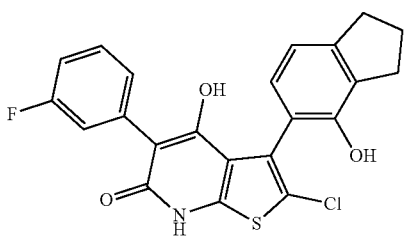

(Ib)

2-chloro-4-hydroxy-3-(4-hydroxyindan-5-yl)-5-phenyl-7H-thieno[2,3-b]pyridin-6-one having Formula (Ic):

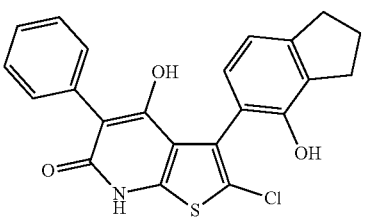

(Ic)

PXL770 may be prepared according to a process comprising the steps of:

(A) reacting a compound of formula (II) with potassium carbonate in a solution comprising water and a solvent selected from n-butyl acetate and isopropanol:

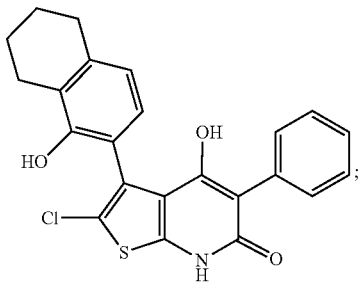

(II)

(B) forming a precipitate; and
(C) recovering the precipitate obtained in step (B), preferably by filtration.

The compound of formula (II) and a preparation process thereof have been disclosed in patent application WO 2014/001554.

Alternatively, said compound of formula (II) may be obtained by an improved process comprising the steps of:

(a) reacting 6-acetyl-5-hydroxytetralin with an electrophilic benzyl source, preferably benzyl bromide, in the presence of a base;
(b) reacting the compound obtained in step (a) with ethyl cyanoacetate in the presence of hexamethyldisilazane and acetic acid;
(c) reacting the compound obtained in step (b) with sulfur in the presence of a base;
(d) optionally forming a salt of the compound obtained in step (c), preferably a hydrochloride salt;
(e) reacting the compound obtained in step (c) or (d) with an electrophilic chlorine source, preferably N-chlorosuccinimide;
(f) reacting the compound obtained in step (e) with phenylacetyl chloride;
(g) reacting the compound obtained in step (f) with a base;
(h) reacting the compound obtained in step (g) with boron tribromide or trichloride, preferably boron trichloride; and
(i) optionally recovering the compound obtained in step (h).

Typically, step (B) can comprise a substep (b1) of heating the mixture obtained in step (A), preferably at a temperature close to reflux of the mixture, followed by a substep (b2) of cooling the resulting mixture, for instance at a temperature comprised between −15° C. and 35° C. The expression "close to reflux of the mixture" refers typically to a temperature comprised between 90% and 100% of the boiling point of the solvent system in step (A) (for instance, water/isopropanol or water/n-butyl acetate).

A distillation step, preferably under reduced pressure, can be carried out between the heating substep and substep (b2).

Step (B) allows a crystalline precipitate to form, which formation may be favored or triggered by adding seeds to steps (b2).

In a preferred embodiment, said precipitate is recovered by filtration in step (C). It may then be washed successively with one or more solvents, preferably water, n-butyl acetate and/or tert-butyl methyl ether.

The compound of formula (Ia), i.e. PXL770, is thus obtained in the form of a solid, such as a powder, having the following XRPD (X-Ray Powder Diffraction) peaks, as measured by means of a diffractometer, using Cu K(alpha) radiation:

| 2-theta (°) | d-value (Å) |
|---|---|
| 13.010 | 6.7992 |
| 14.720 | 6.0130 |
| 17.330 | 5.1128 |
| 19.640 | 4.5164 |
| 21.170 | 4.1933 |
| 22.700 | 3.9140 |
| 23.860 | 3.7263 |
| 24.410 | 3.6435 |
| 26.730 | 3.3323 |
| 28.700 | 3.1079 |
| 30.960 | 2.8860 |
| 34.750 | 2.5794 |
| 35.530 | 2.5246 |
| 35.950 | 2.4960 |
| 36.660 | 2.4493 |

An object of the present invention is a method for treating diseases selected from the group consisting of adrenoleukodystrophy and adrenomyeloneuropathy, the method comprising administering to a subject in need thereof an effective amount of a thienopyridone derivative of formula (I) or a pharmaceutical composition comprising an effective amount of a thienopyridone derivative of formula (I) and a pharmaceutically acceptable support.

The invention furthermore relates to the use of a thienopyridone derivative of formula (I), or a composition comprising the same, in the manufacture of a medicament for the treatment of adrenoleukodystrophy and/or adrenomyeloneuropathy.

The thienopyridone derivatives of formula (I) appear to treat ALD and/or AMN through the reduction of the accumulation of VLCFAs. Indeed, it has been shown in the literature that VLCFA load increases with severity of the disease and lowering of VLCFA can abrogate the inflammatory response. Hence lowering VLCFA overload, especially in the central nervous system, has potential to halt or reverse the disease progression in ALD and/or AMN.

The inventors have found that the thienopyridone derivatives of formula (I) strongly decrease the level of VLCFA in ALD and AMN patient-derived fibroblasts and lymphocytes and in mouse-mixed glial cells. The thienopyridone derivatives of formula (I) act on the restoration of ALDP (ABCD1) function by inducing the overexpression of ABCD2, also known as ALDRP, which has significant sequence similarity with ALDP. The inventors have found that the thienopyridone derivatives of formula (I) induce the overexpression of ABCD2, which compensates for the lack of ABCD1 and thus allows the reduction of the accumulation of VLCFA.

The pharmaceutical composition used according to the invention may be prepared by any conventional method. The thienopyridone derivative of formula (I) can be converted into a suitable dosage form here together with at least one solid, liquid and/or semi-liquid excipient or adjuvant and, if desired, in combination with one or more further active ingredients.

The term "pharmaceutically acceptable support" refers to carrier, adjuvant, or excipient acceptable to the subject from a pharmacological/toxicological point of view and to the manufacturing pharmaceutical chemist from a physical/chemical point of view regarding to composition, formulation, stability, subject acceptance and bioavailability.

The term "carrier", "adjuvant", or "excipient" refers to any substance, not itself a therapeutic agent, that is added to a pharmaceutical composition to be used as a carrier, adjuvant, and/or diluent for the delivery of a therapeutic agent to a subject in order to improve its handling or storage properties or to enable or facilitate formation of a dosage unit of the composition into a discrete article. The pharmaceutical compositions of the invention, either individually or in combination, can comprise one or several agents or vehicles chosen among dispersants, solubilisers, stabilisers, preservatives, etc.

The terms "treatment", "treating" and "treat" refer to therapy, prevention and prophylaxis of a disorder selected in the group consisting of adrenoleukodystrophy (ALD) and adrenomyeloneuropathy (AMN). As disclosed herein, the term "treatment" or "treating" refers to the prophylaxis of a disease or at least one of its symptoms. This also means an improvement, prevention of at least one measurable physical parameter associated with the disease being treated, which is discernible or not in the subject. The term "treatment" or "treating" further refers to inhibiting or slowing the progression of the disease, physically, stabilization of a discernible symptom, physiologically, for example, stabilization of a physical parameter, or both. The term "treatment" or "treating" also refers to delaying the onset of a disease or disorder. In some particular embodiments, the compound of the invention is administered as a preventive measure. In this context, "prevention" or "preventing" refers to a reduction in the risk of developing at least one of the symptoms related to the disease.

The term "treating" can include acting on the accumulation of very long-chain fatty acids (VLCFAs) with a thienopyridone derivative of formula (I) or a pharmaceutical composition comprising the same. More specifically, the thienopyridone derivatives of formula (I) reduce VLCFAs accumulation and thus can abrogate or reduce the inflammatory response. "Treatment," as used herein, also covers any treatment of central demyelination, adrenocortical insufficiency or adrenal gland dysfunction. Thus, the terms "treat", "treating," "treatment," and the like, include the treatment of symptoms related to ALD and/or AMN.

The treatment involves the administration of a thienopyridone derivative of formula (I) or a pharmaceutical composition of the invention to a subject having a declared disorder to cure, delay, or slow down the progress, thus improving the condition of patients.

Within the context of the invention, the term "subject" means a mammal and more particularly a human. The subjects to be treated according to the invention can be appropriately selected on the basis of several criteria associated to the disease such as previous drug treatments, associated pathologies, genotype, exposure to risk factors, viral infection, as well as any other relevant biomarker that can be evaluated by means of immunological, biochemical, enzymatic, chemical, or nucleic acid detection method.

In the case of ALD, the treatment is more particularly suitable for a patient being from 2 to 10 years old. As AMN is an adult form of ALD, the treatment is more particularly suitable for a patient being between 20 and 39 years old.

Pharmaceutical compositions can be administered in the form of dosage units which comprise a predetermined effective amount of active ingredient per dosage unit.

Pharmaceutical compositions can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such compositions can be prepared using all processes known in the pharmaceutical art by, for example, combining the active ingredient with the excipient(s) or adjuvant(s). Preferably, the pharmaceutical composition according to the invention is adapted for oral administration.

Pharmaceutical compositions adapted for oral administration can be administered as separate units, such as, for example, capsules or tablets; powders or granules; solutions or suspensions in aqueous or non-aqueous liquids; edible foams or foam foods; or emulsions, such as oil-in-water liquid emulsions or water-in-oil liquid emulsions.

Thus, for example, in the case of oral administration in the form of a tablet or capsule, the active ingredient component can be combined with an oral, non-toxic and pharmaceutically acceptable inert excipient. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules may be produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The compound according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Pharmaceutical compositions adapted for oral administration can also be formulated by spray drying of a solid or liquid dispersion.

Oral liquids, such as, for example, solution, syrups and elixirs, can be prepared in the form of dosage units so that a given quantity comprises a prespecified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The thienopyridone derivative used according to the invention can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

By "effective amount" it is meant the quantity of the compound as defined above which prevents, removes or reduces the deleterious effects of the treated disease in humans. It is understood that the administered dose may be adapted by those skilled in the art according to the patient, the pathology, the mode of administration, etc. For instance, the thienopyridone derivative of formula (I) may be administered once or twice a day at a daily dose of 0.5 mg to 300 mg for a human patient, preferably from 20 mg to 1000 mg, more preferably from 60 mg to 500 mg. It can be administered 4, 5, 6 or 7 days a week as a long-life medication.

In a particular embodiment of this invention, the thienopyridone derivative of formula (I) is administered as dosage units which comprise from 0.5 mg to 1500 mg, preferably from 20 mg to 1000 mg, more preferably from 60 mg to 500 mg of the thienopyridone derivative of formula (I).

The invention will also be described in further detail in the following examples, which are not intended to limit the scope of this invention, as defined by the attached claims.

EXAMPLES

Example 1: Synthesis of PXL770

Abbreviations
a/a: ratio of the peak area of a given compound to the total of the peak areas on a spectrum or a chromatogram.
eq: equivalent
Analytical Methods
XRPD
X-Ray Powder Diffraction (XRPD) analyses were performed using a Panalytical Xpert Pro diffractometer equipped with a Cu (K alpha radiation) X-ray tube and a Pixcel detector system. The samples were analysed in transmission mode and held between low density polyethylene films. XRPD patterns were sorted, manipulated and indexed using HighScore Plus 2.2 c software.

TG/DTA

Thermogravimetric (TG) analyses were carried out on a Perkin Elmer Diamond Thermogravimetric/Differential Temperature Analyser (TG/DTA). The calibration standards were indium and tin. Samples were placed in an aluminium sample pan, inserted into the TG furnace and accurately weighed. The samples were heated from 30-300° C. in a stream of nitrogen at a rate of 10° C./minute. The temperature of the furnace was equilibrated at 30° C. prior to the analysis of the samples.

1a) Synthesis of 1-(5-benzyloxytetralin-6-yl)ethanone (1)

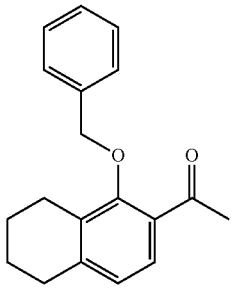

(1)

6-Acetyl-5-hydroxytetralin (100 g, 1 eq.) was dissolved in acetonitrile (300 mL). After addition of $K_2CO_3$ (1.1 eq.) and benzyl bromide (1.05 eq.), the suspension was heated (76° C.). After 48 hours, benzyl bromide (0.1 eq.) was added. After overall 74 hours, the solid was filtered off and washed with acetonitrile (200 mL), and the combined filtrates were evaporated. Compound 1 was obtained as a syrup: m=148.6 g, quantitative yield, 96.6% a/a purity.

1b) Synthesis of ethyl 2-amino-4-(5-benzyloxytetralin-6-yl)thiophene-3-carboxylate (2)

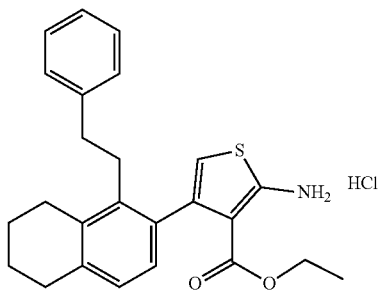

(2)

Acetic acid (70 mL) was heated to T=65° C. HMDS (1.5 eq.) was added over 10 min. Afterwards, a solution of compound 1 (69.5 g, 1 eq.) and ethyl cyanoacetate (1.5 eq.) in acetic acid (140 mL) was added. The resulting mixture was stirred at T=65° C. for 24 h.

After cooling to room temperature, aqueous NaOH (1 M, 140 mL) and TBME (210 mL) were added. The layers were separated. The organic layer was washed with aqueous NaOH (1 M, 4×140 mL) until the pH of the aqueous phase was basic (pH=13). The organic layer was washed with aqueous HCl (1 M, 140 mL) and $H_2O$ (2×140 mL).

EtOH (240 mL), $NaHCO_3$ (1.3 eq.) and sulfur (1.0 atom eq.) were added. After heating to reflux for 180 min, the reaction mixture was concentrated to 210 mL and co-evaporated with TBME (3×140 mL). After cooling to room temperature, the suspension was filtered and the solid was washed with TBME (70 mL). The combined filtrates were concentrated to 210 mL and HCl in dioxane (1.1 eq.) was added dropwise at room temperature. After seeding, precipitation was observed. Heptane (350 mL) was added dropwise at room temperature. After stirring for 14 h, the suspension was filtered. After washing with heptane (3×70 mL) and drying, compound 2 was recovered as a solid. m=83.2 g, 71% yield, 93.7% a/a purity.

1c) Synthesis of ethyl 4-(5-benzyloxytetralin-6-yl)-5-chloro-2-[(2-phenylacetyl)amino]thiophene-3-carboxylate (3)

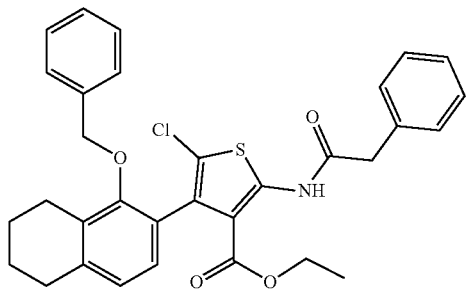

(3)

Compound 2 (17.69 g, 1 eq.) was dissolved in dichloromethane (140 mL). The resulting solution was cooled with ice/water. Under stirring, N-chlorosuccinimide (1.05 eq.) was added. The mixture became dark over a few minutes. After 1 h, phenylacetyl chloride (1.25 eq.) was added.

After 1 hour at 0° C. and 2 hours at room temperature, the mixture was evaporated down to ca. 35 mL and EtOH (2×70 mL) was added, and evaporated down again. The mixture was diluted with EtOH (35 mL) and cooled with ice/water. The product precipitated. The solid was filtrated and washed with cold EtOH (3×18 mL).

Compound 3 was obtained as a solid: m=20.99 g, 94.2% yield, 99.3% a/a purity.

1d) Synthesis of 3-(5-benzyloxytetralin-6-yl)-2-chloro-4-hydroxy-5-phenyl-7H-thieno[2,3-b]pyridin-6-one (4)

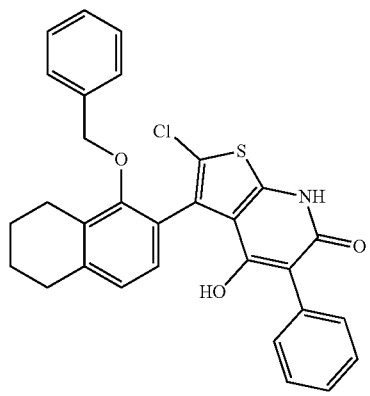

(4)

Compound 3 (19.88 g, 1 eq.) was solubilized in methyltetrahydrofuran (120 mL), and the reaction mixture was cooled to a temperature between −16° C. and −10° C. (NaCl/Ice). Potassium tert-butoxide (5 eq.) was added in four portions. Then, the reaction mixture was warmed up to room temperature, and stirred for 65 min at room temperature. A dropwise addition of 2 N HCl (5 eq.) was carried out at T=0-5° C. (water/ice) and the resulting mixture was stirred vigorously. The organic phase was washed with NaCl$_{(aq)}$ (11%, 1×50 mL) and water (2×50 mL). The organic phase was concentrated to ~50% solution. Methyltetrahydrofuran (80 mL) was added, and the resulting solution was concentrated to ~50% solution. TBME (100 mL) was added, and the resulting solution was concentrated to ~50% solution (this step was repeated 3 times). Then, TBME (25 mL), seeds of compound 4 and n-Heptane (20 mL) were added and the resulting solution was stirred at room temperature overnight. The mixture was concentrated to ca. 50 mL, filtrated, rinsed with mother liquor and washed with n-Heptane (2×40 mL) and dried. Compound 4 was obtained as a granular solid. Yield 88%, 99.5% a/a purity.

1e) Synthesis of 2-chloro-4-hydroxy-3-(5-hydroxytetralin-6-yl)-5-phenyl-7H-thieno[2,3-b]pyridin-6-one (I)

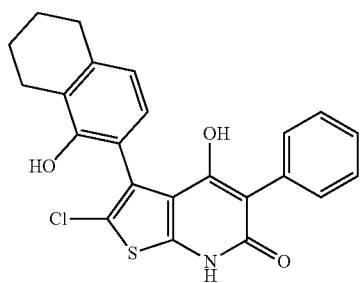

(I)

Compound 4 (15 g, 1 eq.) was dissolved in 75 mL of dichloromethane and was cooled to T=−10° C./−15° C. (with ice/NaCl). BCl$_3$ (1.5 eq., solution: 1 mol/L in dichloromethane) was added dropwise and the resulting mixture was stirred at room temperature for 15 hours. The resulting mixture was cooled with ice/water, and water (75 mL) was added. The resulting mixture was stirred vigorously and the organic phase was extracted with water/MeOH (9:1 v/v, 5×45 mL.). The organic phase was concentrated, a solvent swap was carried out with toluene (3×90 mL) and diluted with toluene to reach a final volume of 90 mL of toluene. The resulting mixture was heated to reflux and 15 mL of methanol was added. A brownish solution with few particles was obtained. Seeds were added at T=40° C., warmed to T=52° C. and cooled to room temperature. The resulting mixture was stirred overnight, and then was cooled with ice/NaCl (T=−10° C./−15° C.) for 100 minutes. The precipitated product was filtrated, washed with toluene/heptane 1:2 v/v (15 mL) and heptane (15 mL) and dried. Crystals of compound (I) were obtained: 87% yield, 99.0% a/a purity.

1f) Synthesis of the monohydrate potassium salt of 2-chloro-4-hydroxy-3-(5-hydroxytetralin-6-yl)-5-Phenyl-7H-thieno[2,3-b]pyridin-6-one (Ia)

Compound (I) was suspended in water/isopropanol mix (1/1, 5 parts of each solvents) then 0.50 to 0.55 eq of potassium carbonate was added. The pH was about 12 (pH indicator paper) at the end of the addition of potassium carbonate. After 3 hours of stirring at 50° C., the suspension was thicker and the pH was about 8 (pH indicator paper). The temperature was raised to 80° C. until a solution was obtained (10-15 minutes). A clarification can be done at this point of the process if required. 7 parts of water were added and the reaction mixture was then cooled to 40° C. (turbid solution observed). The solvent was distilled under reduce pressure (from 180 mbar to 40 mbar) at 40° C. until 7 parts of solvents remained in the reactor. Crystallization of potassium salt monohydrate may occur here. 4.2 parts of water were added and the mixture was seeded with compound (I) (1 to 2% of seeds). The suspension was then cooled down from 40° C. to 5° C. in 7 hours (5° C./hour) and kept at 5° C. for several hours. The suspension was filtered. The cake was washed twice by 1.42 parts of water. The collected solid was dried at 40° C. under vacuum given minimum 80% yield of Compound (Ia), at required chemical purity (i.e. 98%+).

Example 2: Characterization of PXL770 a) X-ray powder diffraction (XRPD) data of compound (Ia) indicated that it was composed of a crystalline material. The XRPD description of compound (Ia) is shown in Table 1.

TABLE 1

| Peak No | 2-theta (°) | d-value (Å) | Relative intensity (%) |
|---|---|---|---|
| 1 | 4.910 | 17.9826 | 15 |
| 2 | 11.560 | 7.6486 | 8 |
| 3 | 13.010 | 6.7992 | 25 |
| 4 | 14.720 | 6.0130 | 100 |
| 5 | 16.450 | 5.3843 | 11 |
| 6 | 17.330 | 5.1128 | 49 |
| 7 | 17.770 | 4.9872 | 14 |
| 8 | 18.690 | 4.7437 | 12 |
| 9 | 19.220 | 4.6141 | 16 |
| 10 | 19.640 | 4.5164 | 20 |
| 11 | 20.190 | 4.3946 | 8 |
| 12 | 21.170 | 4.1933 | 23 |
| 13 | 21.580 | 4.1145 | 12 |
| 14 | 22.190 | 4.0028 | 12 |
| 15 | 22.700 | 3.9140 | 26 |
| 16 | 23.240 | 3.8243 | 17 |
| 17 | 23.860 | 3.7263 | 23 |
| 18 | 24.410 | 3.6435 | 43 |
| 19 | 25.330 | 3.5133 | 10 |
| 20 | 26.230 | 3.3947 | 17 |
| 21 | 26.730 | 3.3323 | 23 |
| 22 | 28.700 | 3.1079 | 25 |
| 23 | 29.590 | 3.0164 | 11 |
| 24 | 29.950 | 2.9810 | 13 |
| 25 | 30.960 | 2.8860 | 36 |
| 26 | 31.570 | 2.8316 | 15 |
| 27 | 32.200 | 2.7776 | 18 |
| 28 | 33.080 | 2.7057 | 14 |
| 29 | 33.530 | 2.6704 | 17 |
| 30 | 34.050 | 2.6308 | 10 |
| 31 | 34.750 | 2.5794 | 26 |
| 32 | 35.530 | 2.5246 | 56 |
| 33 | 35.950 | 2.4960 | 22 |
| 34 | 36.660 | 2.4493 | 20 |
| 35 | 37.300 | 2.4087 | 11 |
| 36 | 38.320 | 2.3469 | 16 |
| 37 | 39.490 | 2.2801 | 13 | b) TG/DTA analysis showed an initial weight loss of 1.1% from 30-100° C., followed by larger weight loss of 3% from 117-160° C. due to loss of bound water. The second weight loss was accompanied by a large endotherm and the combined weight losses of 4% approximate the theoretical weight loss for a monohydrate (3.75% w/w). The compound decomposed above 240° C.

Example 3: Decrease in the Levels of Very Long Chain Fatty Acids (VLCFA) in AMN Patient-Derived Lymphocytes Treated with PXL770

Accumulation of very long chain fatty acids (VLCFA) in the plasma and tissues (including the brain and spinal cord) is a hallmark of AMN disease. It has been shown in the literature that VLCFA load increases with severity of the disease and lowering of VLCFA can abrogate the inflammatory response. Hence lowering VLCFA overload, especially in the central nervous system, has potential to halt or reverse the disease progression in AMN.

In order to show the efficacy of PXL770 to lower very long chain fatty acids (VLCFA) in vitro, the study focuses on the level assessment of the hexacosanoic acid, which is the most prevalent VLCFA, in healthy control cells and in AMN human patient-derived primary lymphocytes. The cell lines were obtained from Coriell Cell Repositories. Lymphocytes were cultured in RPMI-1640 with 10% fetal bovine serum (FBS). The cultures were split in 1:5 ratio. Lymphocytes from healthy patients were used as control. All treatments were in complete media containing fetal bovine serum (FBS, 15%). All cultured cells were maintained at 37° C. in 5% $CO_2$.

VLCFA content was then measured as follows. Samples are adjusted to a final volume of 0.5-1 ml with LC-MS grade water and spiked with 10 ng of Lignoceric acid-d4 as an internal standard. The sample is acidified to pH 3-4 with dilute hydrochloric acid and extracted with isooctane-ethyl acetate (9:1) three times with equal volume. The extract is dried under nitrogen and the residue is reconstituted in methanol-water-ammonium acetate (75:25:10 mM).

Total fatty acids: After preparing the samples with internal standard as described above for free fatty acids, aqueous sodium hydroxide is added to a final concentration of 1 M. The mixture is incubated at 37° C. in dark under nitrogen for 3 h. The samples are then acidified, extracted, and reconstituted as described above.

LC-MS analysis of fatty acids: The reconstituted fatty acid extracts are subjected to HPLC on Targa C8 column (2×10 mm) using methanol-aqueous ammonium acetate (10 mM) solvent mixture. The column is eluted with a gradient of methanol (75 to 90%) over 8 min at a flow rate of 0.25 ml/min. The column eluent is directly introduced to mass analyzer (QTRAP5500) and monitored for fatty acids using published pseudo MRM method. Under these conditions, the VLCFA elute between 5 and 8 min. Each fatty acid is quantitated against the added internal standard.

First, the evolution of hexacosanoic acid in lymphocytes is monitored in healthy control cells and in AMN human patient-derived primary lymphocytes; and in a second time a treatment of PXL770 was assigned to AMN human-derived primary lymphocytes in culture at different concentrations (5 µM, 10 µM, 25 µM, 50 µM) for one week and the level of hexacosanoic acid was measured.

Figure 1:
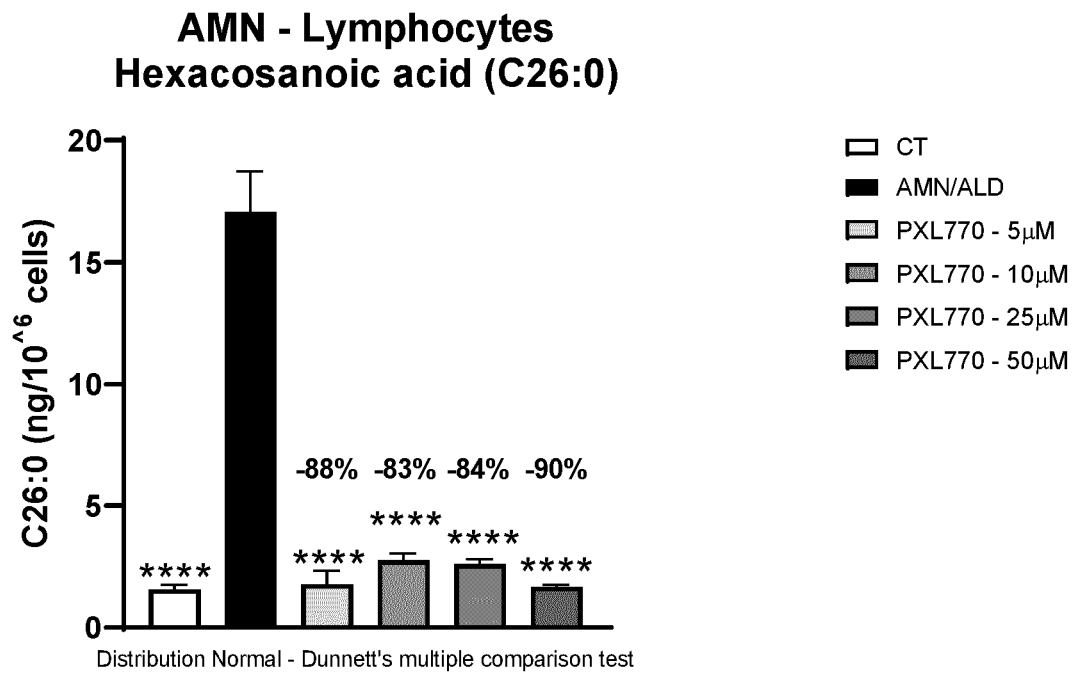
FIG. 1 shows the level of hexacosanoic acid in AMN patient-derived lymphocytes when they are treated or not with PXL770.
Six situations were studied: Healthy control/AMN without treatment/AMN+PXL770 (5 μM)/AMN+PXL770 (10 μM)/ AMN+PXL770 (25 μM)/AMN+PXL770 (50 μM).

Results of this study are presented in FIG. 1. This figure shows that the level of hexacosanoic acid (expressed as ng per $10^6$ cells) decreases in lymphocytes of AMN patients when they are treated with different doses of PXL770. PXL770 at all doses tested strongly decreases the level of hexacosanoid acid and reaches at the doses of 5 and 50 µM to the same level as that present in lymphocytes of healthy controls.

In conclusion, it can be confirmed that PXL770 strongly decreases the level of hexacosanoic acid and more broadly the most prevalent VLCFAs in AMN patient-derived lymphocytes.

Example 4: Overexpression of ABCD2 in AMN Fibroblasts Cultured in the Presence of PXL770

Therapeutic investigations in AMN have also focused on induction of functionally redundant peroxisomal transporter adrenoleukodystrophy-related protein (ABCD2, also known as ALDRP). ABCD2 has significant sequence similarity with ABCD1 (also known as ALDP), the gene mutated/deleted in AMN and therefore, can compensate for ABCD1 loss when over-expressed.

In order to show that the presence of PXL770 in the culture of AMN fibroblasts increase the expression of ABCD2 levels, a western blot was performed to compare the levels of ABCD2 in AMN fibroblasts in the absence and in the presence of PXL770. More specifically, protein extraction was performed as follows.

The cells were washed with cold Tris-buffered saline (20 mM Trizma base and 137 mM NaCl, pH 7.5) and lysed in 1×SDS sample-loading buffer (62.5 mM Trizma base, 2% [w/v] SDS, 10% glycerol), and after sonication and centrifugation at 15,000 g for 5 min, the supernatant was used for the immunoblot assay. The protein concentration of samples was determined with the detergent compatible protein assay reagent (Bio-Rad) using BSA as the standard. The sample was boiled for 3 min with 0.1 volumes of 10% β mercaptoethanol and 0.5% bromphenol blue mix. Then, 40 µg of total cellular protein was resolved by electrophoresis on 8 or 12% polyacrylamide gels, electrotransferred and blocked with Tween 20-containing Tris-buffered saline (TBST; 10 mM Trizma base, pH 7.4, 1% Tween 20, and 150 mM NaCl) with 5% skim milk. After incubation with antibodies against ABCD2, ABCD3, and (β-actin at 4° overnight, the membranes were then washed with TBST and incubated with horseradish peroxidase-conjugated anti-rabbit or mouse IgG for 1 h at room temperature. The membranes were detected by autoradiography using ECL-plus (Amersham Biosciences) after washing with TBST buffer.

Figure 2:
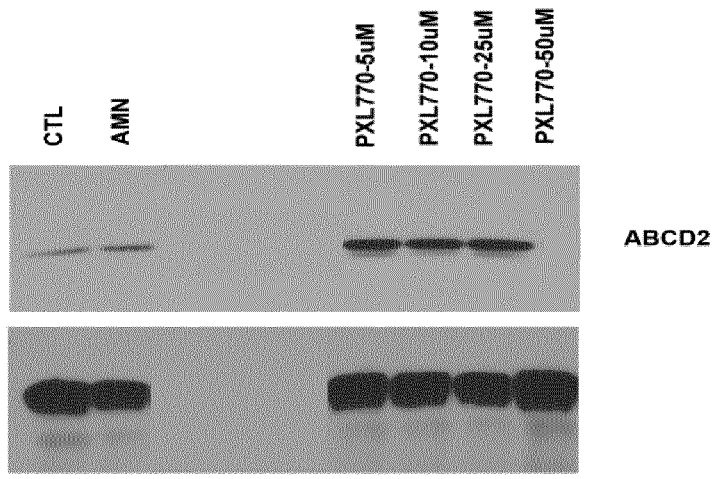
FIG. 2 shows the level of expression of ABCD2 in AMN fibroblasts when they are cultured with or without the presence of PXL770.

The results of Western blot analysis are presented in FIG. 2. This figure allows us to ensure that there is an overexpression of the proteins ABCD2 in AMN fibroblasts when they are treated with PXL770 at concentrations of 5, 10, 25 µM compared to their level in control fibroblasts and more interestingly compared to AMN fibroblasts not treated with PXL770.

It was known in the literature that over-expression of ABCD2 leads to reduced VLCFA accumulation in cultured fibroblasts from AMN patients (Kemp S., Wei H. M., Lu J. F., Braiterman L. T., McGuinness M. C., Moser A. B., Watkins P. A. and Smith K. D. (1998) Gene redundancy and pharmacological gene therapy: implications for X-linked adrenoleukodystrophy. Nat. Med. 4, 1261-1268).

Consequently, PXL770 induces the overexpression of ABCD2, which can thus compensate for the lack of ABCD1 and thus allows for one or both of these alternative proteins to contribute to the reduction of the accumulation of VLCFA.

Example 5: Decrease in the Levels of Very Long Chain Fatty Acids (VLCFA) in AMN Mouse-Mixed Glial Cells The inventors carried out a study of the measurement of VLCFA accumulation in AMN mouse-mixed glial cells when they are not undergoing any treatment and when they are treated with PXL770 at different doses.

C57BL6 mouse breeding pairs were purchased from Jackson Laboratory (Bar Harbor, ME) and maintained at the Henry Ford Health System (HFHS) animal facility. All animal procedures were approved by the HFHS Animal Review Committee and all animals received humane care in compliance with the HFHS experimental guidelines and the National Research Council's criteria for humane care (Guide for Care and Use of Laboratory Animals). Mouse with Abcd1 gene knocked-out were raised and used to extract mixed glial cells. Primary astrocyte-enriched cultures were prepared from the whole cortex of 1-day-old C57BL/6 mice. Briefly, the cortex was rapidly dissected in ice-cold calcium/magnesium-free HBSS at pH 7.4 as described previously. The tissue was minced, incubated in HBSS containing trypsin (2 mg/ml) for 20 min, and washed twice in plating medium containing 10% FBS and 10 µg/ml gentamicin and then disrupted by triturating through a Pasteur pipette, after which cells were seeded in 75-cm$^2$ culture flasks (Falcon, Franklin, NJ). After incubation at 37° C. in 5% $CO_2$ for 1 day, the medium was completely changed to the culture medium (DMEM containing 10% FBS and 10 µg/ml gentamicin). The cultures received half exchanges with fresh medium twice a week. All cultured cells were maintained at 37° C. in 5% $CO_2$. After 10 days confluent mixed glial cultures were used for the outlined experiments.

Hexacosanoic acid level in six groups of mixed glial cells was measured. These six groups include wild type mixed glial cells, ALD-KO mixed glial cells (which corresponds to AMN mouse-derived glial cells, ALD is another name for ABCD1), and ALD-KO mixed glial cells with a treatment of different concentrations of PXL770 (5 µM, 10 µM, 25 µM, 50 µM).

Figure 3:
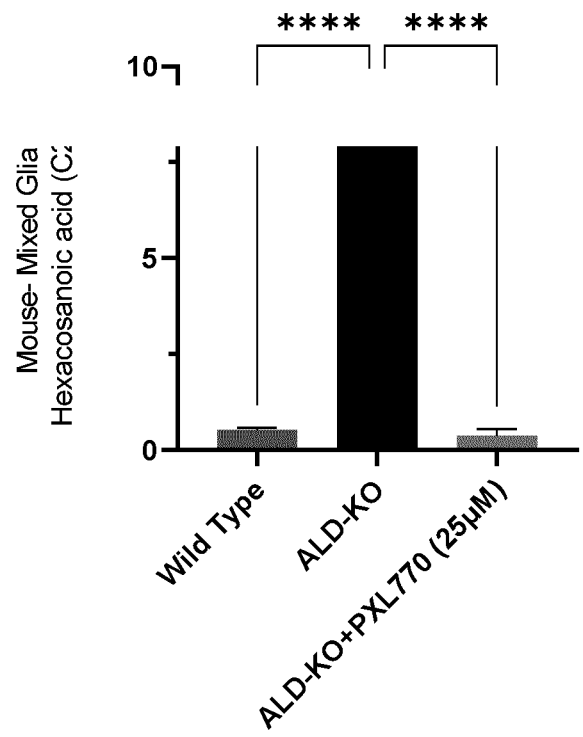
FIG. 3 shows the level of hexacosanoic acid in AMN mouse-mixed glial cells when they are treated or not with PXL770.
Three situations were studied: Wild Type/ALD-KO/ALD-KO+PXL770 (25 μM).

The results are shown in FIG. 3. When ALD-KO mouse-mixed glial cells are cultured in the presence of PXL770 (25 µM), the accumulation of hexacosanoic acid in these cells decreases. In conclusion, PXL770 plays a role in reducing accumulation of hexacosanoic acid and more broadly of VLCFA in general.

Example 6: Overexpression of ABCD2 in ALD-KO Mouse Brain Cortex Mixed Glial Cells in the Presence of PXL770

The same experimental protocol as in example 4 was performed for ALD-KO mouse brain cortex mixed glial cells. This model is mainly a model for AMN.

Figure 4:
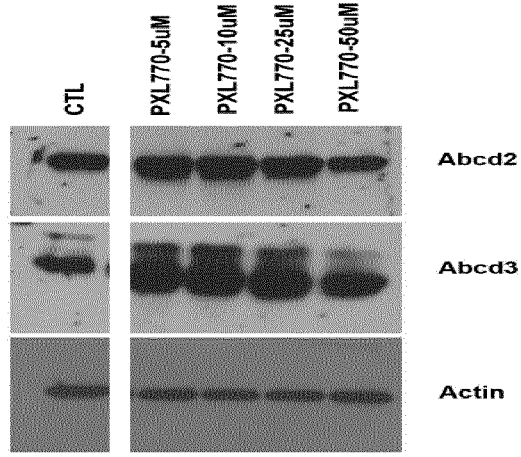
FIG. 4 shows the level of expression of ABCD2 in ALD-KO mouse brain cortex mixed glial cells when they are cultured with or without the presence of PXL770.

FIG. 4 shows that, as in AMN patient-derived fibroblasts of example 4, there is an overexpression of ABCD2 when ALD-KO mouse brain cortex mixed glial cells were treated with PXL770 compared to non-treated ALD-KO mouse brain cortex mixed glial cells (ctl).

In conclusion, PXL770 up-regulated ABCD2 level in ALD-KO mouse brain cortex mixed glial cells.

Example 7: Decrease in the Levels of Very Long Chain Fatty Acids (VLCFA) in ALD Patient-Derived Lymphocytes Treated with PXL770

After studies on cells from patients with the most severe form of ALD (AMN) the inventors replicated the same study method as in example 1 to analyze the effect of PXL770 on cells from X-ALD patients (severe inflammatory phenotype).

Figure 5:
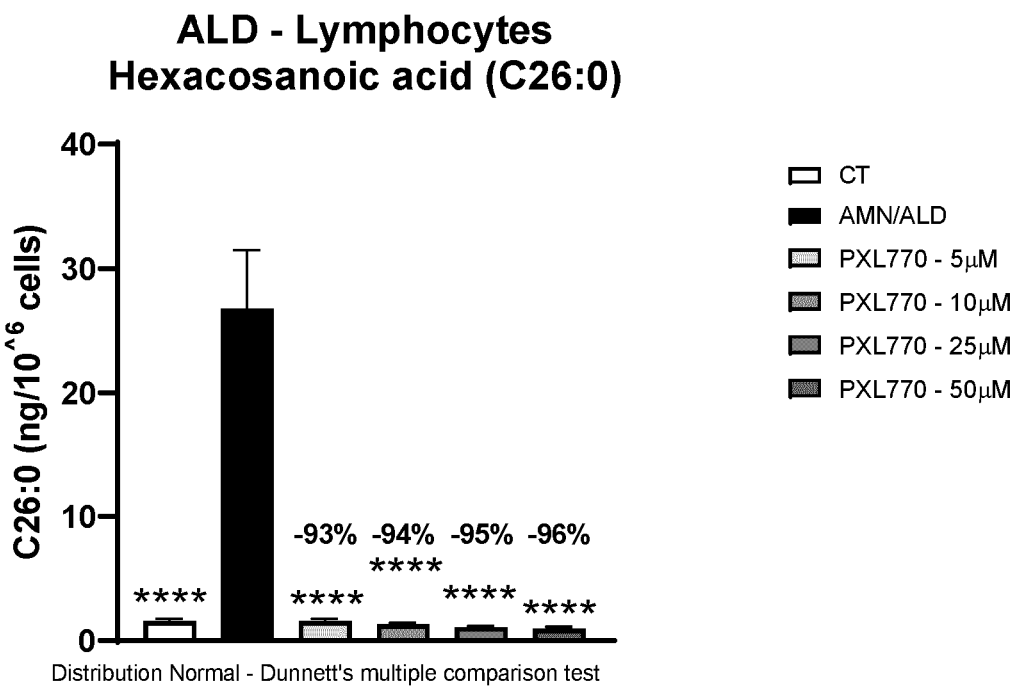
FIG. 5 shows the level of hexacosanoic acid in ALD patient-derived lymphocytes when they are treated or not with PXL770.

The results that are presented in FIG. 5 show that the level of hexacosanoic acid decreases in lymphocytes of ALD patients when they are treated with increasing concentrations of PXL770 reaching the same level as that present in lymphocytes of healthy controls.

PXL770 strongly decreases the level of VLCFA in ALD patient-derived lymphocytes.

Example 8: Overexpression of ABCD2 in ALD Fibroblasts Cultured in the Presence of PXL770

In the same way as example 4, in order to show that the presence of PXL770 in the culture of ALD patient fibroblasts increases the expression of ABCD2 levels, a Western blot was performed to compare the levels of ABCD2 in ALD patient fibroblasts in the absence and in the presence of PXL770.

The result of the Western blot is presented in FIG. 6. These results show that there is an overexpression of the proteins ABCD2 in ALD fibroblasts when they are treated with PXL770, especially with low concentration of PXL770 (5 µM).

In conclusion, PXL770 can compensate for the lack of ABCD1 and thus contribute to the reduction of the accumulation of VLCFA.

Example 9: In Vivo Experiment on X-ALD Mouse

Male ABCD1-KO mice (n=15) were treated with oral gavage of PXL770 (75 mg/kg) twice a day, every day for 60 days. Untreated ABCD1-KO mice (n=15) and wild-type (WT) mice (n=12) served as controls. Post-treatment mice were sacrificed and brain cortex and plasma were collected for VLCFA analysis. The analysis was performed according to the standardized protocols of the Lipidomics Core Facility and data are expressed as VLCFA µg/ml levels. Hexacosanoic acid (C26:0) was selected as representative for VLCFAs.

A one-way ANOVA with Dunnett's multiple comparison test was performed to assess the effect of PXL770 on brain's VLCFAs (** $p<0.0001$, * $p<0.001$). A Kruskal-Wallis test with Dunn's multiple comparison test was performed to assess the effect of PXL770 on plasma's VLCFAs (** $p<0.0001$, * $p<0.01$).

As shown on FIGS. 7 and 8, PXL770 significantly reduces VLCFA accumulation both in the brain cortex and in the plasma of X-ALD mice, respectively.

Example 10: Decrease in the Levels of Very Long Chain Fatty Acids (VLCFA) in AMN and ALD Patient-Derived Lymphocytes Treated with Metformin The experiments described in Examples 3 and 7 were performed with metformin by the same lab and described by Singh et al. in Journal of Neurochemistry, 2016; 138, 86-100.

The results of these experiments are shown on FIG. 9.

It was observed that metformin at 5 mM decreased VLCFA content in AMN and ALD patient's derived lymphocytes by −29% and −42%, respectively, after 7 days of treatment, which was not sufficient to provide a normalization effect as shown on FIG. 9 (the VLCFA content remained higher than with the control).

On the contrary, PXL770, when administering at a much lower concentration (5 µM) provided a normalization effect both in AMN patients (see Example 3) and in ALD patients (see Example 7).

This example thus demonstrates that PXL770 decreases VLCFA content in AMN and ALD patient's derived cells with a higher efficacy and a higher potency than metformin.

Example 11: Head-to-Head Comparison Between PXL770 and Metformin

In order to compare the efficacy of PXL770 and metformin to lower very long chain fatty acids (VLCFA) in vitro, the study focuses on the level assessment of the hexacosanoic acid, which is the most prevalent VLCFA, in healthy control cells and in AMN human patient-derived primary fibroblasts. The cell lines were obtained from Coriell Cell Repositories. Fibroblasts were cultured in DMEM with 15% FBS. The cultures were split in 1:5 ratio. Fibroblasts from healthy patients were used as control. All treatments were in complete media containing fetal bovine serum (FBS, 15%). All cultured cells were maintained at 37° C. in 5% $CO_2$.

VLCFA content was then measured as follows. Samples are adjusted to a final volume of 0.5-1 ml with LC-MS grade water and spiked with 10 ng of Lignoceric acid-d4 as an internal standard. The sample is acidified to pH 3-4 with dilute hydrochloric acid and extracted with isooctane-ethyl acetate (9:1) three times with equal volume. The extract is dried under nitrogen and the residue is reconstituted in methanol-water-ammonium acetate (75:25:10 mM).

Total fatty acids: After preparing the samples with internal standard as described above for free fatty acids, aqueous sodium hydroxide is added to a final concentration of 1 M. The mixture is incubated at 37° C. in dark under nitrogen for 3 h. The samples are then acidified, extracted, and reconstituted as described above.

LC-MS analysis of fatty acids: The reconstituted fatty acid extracts are subjected to HPLC on Targa C8 column (2×10 mm) using methanol-aqueous ammonium acetate (10 mM) solvent mixture. The column is eluted with a gradient of methanol (75 to 90%) over 8 min at a flow rate of 0.25 ml/min. The column eluent is directly introduced to mass analyzer (QTRAP5500) and monitored for fatty acids using published pseudo MRM method. Under these conditions, the VLCFA elute between 5 and 8 min. Each fatty acid is quantitated against the added internal standard.

The study planned different groups of patients. First, the evolution of hexacosanoic acid in fibroblasts is monitored in healthy control cells and in AMN human patient-derived primary fibroblasts; and in a second time a treatment of PXL770 was assigned to AMN human-derived primary fibroblasts in culture at different doses (PXL770: 0.1, 0.5, 1, 2, 3.5 and 5 µM; metformin: 100, 200, 300 and 400 µM) for one week and the level of hexacosanoic acid was measured.

The results of this study are presented in FIG. 10. This figure shows that the level of hexacosanoic acid (expressed as ng per $10^6$ cells) decreases in fibroblasts of AMN patients when they are treated with increasing doses of PXL770. In addition, a much higher potency and efficacy is reached with PXL770 compared to metformin.

Example 12: Overexpression of ABCD2 in AMN and ALD Patient's Fibroblasts Cultured in the Presence of Metformin The experiments described in Examples 4 and 6 were performed with metformin by the same lab and described by Singh et al. in Journal of Neurochemistry, 2016; 138, 86-100.

The results of these experiments are shown on FIG. 11.

It was observed that metformin at a very concentration of 5 mM only slightly increased ABCD2 protein expression in AMN and ALD patient's derived fibroblasts.

On the contrary, PXL770, when administered at a much lower concentration (5 µM) provided a much greater effect. PXL770 has thus higher efficacy and potency than metformin.

Example 13: Overexpression of ABCD2 in AMN-KO Mouse Brain Cortex Mixed Glial Cells in the Presence of Metformin The same experimental protocol as in example 6 was performed with metformin by the same lab and described by Singh et al. in Journal of Neurochemistry, 2016; 138, 86-100.

The results of these experiments are shown on FIG. 12.

It was observed that metformin at 100 µM induced limited increase in ABCD2 protein levels in ABCD1-KO mice glial cells.

On the contrary, PXL770, when administered at a much lower concentration (5 µM) provided a much greater effect. PXL770 has thus higher efficacy and potency than metformin.

Example 14: In Vivo Experiment on X-ALD Mouse

Male ABCD1-KO mice (n=8) were treated with oral gavage of PXL770 (75 mg/kg) twice a day, every day for 90 days. Untreated ABCD1-KO mice (n=8) and wild-type (WT) mice (n=8) served as controls. Post-treatment mice were sacrificed and spinal cord was collected for VLCFA analysis. The analysis was performed according to the standardized protocols of the Lipidomics Core Facility and data are expressed as VLCFA µg/ml levels. Hexacosanoic acid (C26:0) was selected as representative for VLCFAs.

As shown on FIG. 13, PXL770 significantly reduces VLCFA accumulation in the spinal cord of X-ALD mice.

Example 15: Decrease in the Levels of Very Long Chain Fatty Acids (VLCFA) in AMN Patient-Derived Fibroblasts Treated with Various Thienopyridones The experiment described in Example 3 was reproduced with various thienopyridone compounds, namely:

The experiment described in Example 3 was reproduced with various thienopyridone compounds, namely:

PXL770: potassium 2-chloro-3-(5-hydroxytetralin-6-yl)-6-oxo-5-phenyl-7H-thieno[2,3-b]pyridin-4-olate PXL700: 2-chloro-4-hydroxy-3-indan-5-yl-5-(3-pyridyl)-7H-thieno[2,3-b]pyridin-6-one PXL702: 2-chloro-4-hydroxy-3-(4-hydroxyindan-5-yl)-5-phenyl-7H-thieno[2,3-b]pyridin-6-one PXL695: 2-chloro-5-(3-fluorophenyl)-4-hydroxy-3-(4-hydroxyindan-5-yl)-7H-thieno[2,3-b]pyridin-6-one, each tested at concentrations from 0.1 to 5 µM.

PXL700 has the following formula:

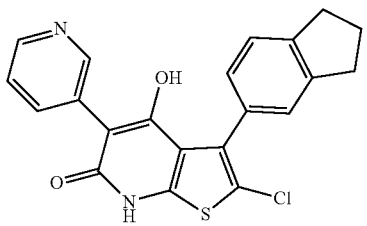 [SMILES: O=c1[nH]c2sc(Cl)c(-c3ccc4c(c3)CCC4)c2c(O)c1-c1cccnc1]

A one-way ANOVA with Dunnett's multiple comparison test was performed to assess the effect of PXL770 on brain's VLCFAs (** $p<0.0001$, * $p<0.001$). A Kruskal-Wallis test with Dunn's multiple comparison test was performed to assess the effect of PXL770 on plasma's VLCFAs (** $p<0.0001$, * $p<0.01$).

As shown on FIG. 14, PXL770, PXL695 and PXL702 exhibited a comparable decrease in VLCFA levels, whereas PXL700 (which is not included within the thienopyridones according to this invention) exhibited no or a very limited effect.

These compounds were further compared at a concentration of 5 µM with metformin at 400 µM. As shown on FIG. 15, metformin also exhibited no or a very limited effect.

The invention claimed is:

1. A method of treating adrenoleukodystrophy and/or adrenomyeloneuropathy comprising administering, to a subject in need of treatment, an effective amount of a compound selected from the group consisting of

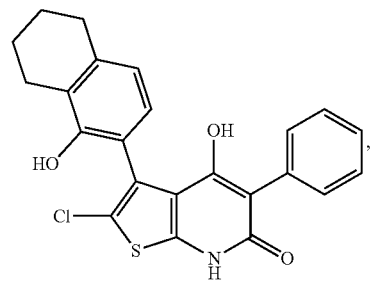
(II)

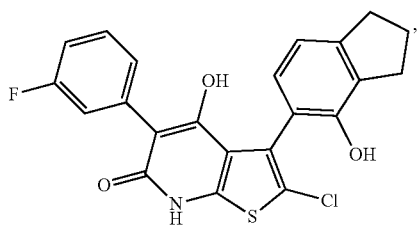
(Ib)

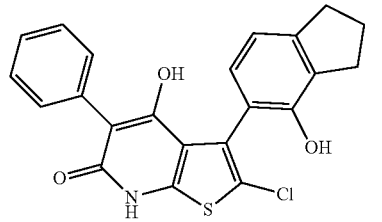
(Ic)

and pharmaceutically acceptable salts and/or solvates thereof.

2. The method of claim 1, wherein said pharmaceutically acceptable salt of said compound is a monohydrate potassium salt of Formula (Ia):

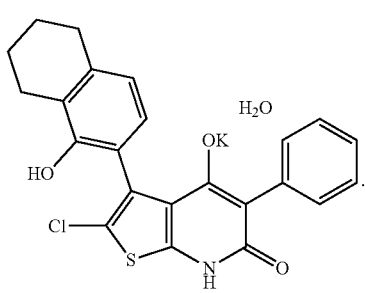
(Ia)

3. The method of claim 1, wherein said compound is administered once or twice a day at a daily dose of 0.5 mg to 3000 mg.

4. The method of claim 1, wherein said subject has central demyelination, adrenocortical insufficiency or adrenal gland dysfunction.

5. The method of claim 1, wherein the compound is administered to an adult for the treatment of adrenomyeloneuropathy.

6. The method of claim 1, wherein the compound is administered to a subject 2 to 10 years of age.

7. The method of claim 1 which is administered orally.

8. The method of claim 1, wherein the compound is administered as a pharmaceutical composition.

9. A method of treating adrenoleukodystrophy comprising administering, to a subject in need of treatment, an effective amount of a compound of Formula (II):

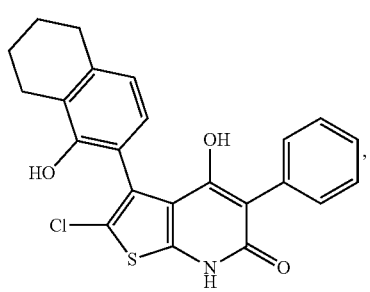
(II)

or a pharmaceutically acceptable salt and/or solvate thereof.

10. The method of claim 9, wherein the compound is administered at a daily dosage from 20 mg to 1000 mg.

11. A method of treating adrenomyeloneuropathy comprising administering, to a subject in need of treatment, an effective amount of a compound of Formula (II):

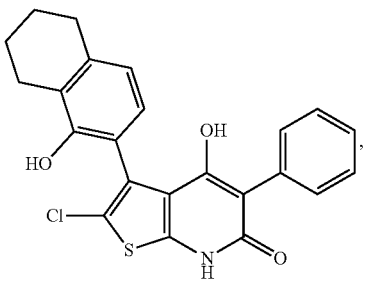

or a pharmaceutically acceptable salt and/or solvates thereof.

12. The method of claim 11, wherein the compound is administered at a daily dosage from 20 mg to 1000 mg.

13. The method of claim 11, wherein an effective amount of a compound of Formula (II) or a pharmaceutically acceptable salt thereof is administered to the subject in need of treatment.

14. The method of claim 9, wherein an effective amount of a compound of Formula (II) or a pharmaceutically acceptable salt thereof is administered to the subject in need of treatment.

15. The method of claim 1, wherein an effective amount of a compound of Formula (II) or a pharmaceutically acceptable salt thereof is administered to the subject in need of treatment.

16. The method of claim 1, wherein an effective amount of a compound of Formula (Ib) or a pharmaceutically acceptable salt thereof is administered to the subject in need of treatment.

17. The method of claim 1, wherein an effective amount of a compound of Formula (Ic) or a pharmaceutically acceptable salt thereof is administered to the subject in need of treatment.

18. The method of claim 3, wherein said compound is administered once or twice a day at a daily dose of 20 mg to 1000 mg.

19. The method of claim 3, wherein said compound is administered once or twice a day at a daily dose of 60 mg to 500 mg.

* * * * *

UNITED STATES PATENT AND TRADEMARK OFFICE
CERTIFICATE OF CORRECTION

| | | |
|---|---|---|
| PATENT NO. | : 11,850,238 B2 | Page 1 of 1 |
| APPLICATION NO. | : 17/914372 | |
| DATED | : December 26, 2023 | |
| INVENTOR(S) | : Sébastien Bolze, Pascale Fouqueray and Sophie Hallakou-Bozec | |

It is certified that error appears in the above-identified patent and that said Letters Patent is hereby corrected as shown below:

In the Specification

Column 18,
Line 36, "and (β-actin" should read --and β-actin--.

Signed and Sealed this
Sixteenth Day of July, 2024

Katherine Kelly Vidal
*Director of the United States Patent and Trademark Office*